US012667402B1

(12) United States Patent
Chien et al.

(10) Patent No.: US 12,667,402 B1
(45) Date of Patent: Jun. 30, 2026

(54) FORCE DETECTION BONE SCREW DEVICE

(71) Applicant: INDUSTRIAL TECHNOLOGY RESEARCH INSTITUTE, Hsinchu (TW)

(72) Inventors: Chih-Wei Chien, Nantou County (TW); Chih-Chieh Huang, Miaoli County (TW); Chun-Chieh Huang, Hsinchu City (TW); Fu-Chiang Jan, Hsinchu City (TW); Shih-Ping Lin, Kaohsiung City (TW); De-Yi Chiou, New Taipei City (TW); Pei-I Tsai, Hsinchu City (TW); Kuo-Kuei Huang, Hsinchu County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 46 days.

(21) Appl. No.: 19/002,833

(22) Filed: Dec. 27, 2024

(30) Foreign Application Priority Data

Dec. 26, 2024 (TW) ................................. 113150800

(51) Int. Cl.
*A61B 17/86* (2006.01)
*H01Q 1/22* (2006.01)
*A61B 17/00* (2006.01)
(52) U.S. Cl.
CPC ......... *A61B 17/864* (2013.01); *H01Q 1/2283* (2013.01); *A61B 2017/00955* (2013.01)
(58) Field of Classification Search
CPC ...................................... A61B 17/86–17/8695
See application file for complete search history.

(56) References Cited

U.S. PATENT DOCUMENTS 5,041,112 A * 8/1991 Mingozzi ........... A61B 17/6416
                                                      606/54
8,721,643 B2 * 5/2014 Morgan ............... A61B 5/0031
                                                      606/62

(Continued)

FOREIGN PATENT DOCUMENTS

CN        103533903 A      1/2014
CN        103945763 B      4/2016

(Continued)

OTHER PUBLICATIONS

Taiwan Patent Office "Office Action" issued on Mar. 6, 2025, Taiwan.

(Continued)

*Primary Examiner* — Zade Coley
(74) *Attorney, Agent, or Firm* — WPAT, PC

(57) ABSTRACT

A force detection bone screw device includes a bone screw body, a spring structure, a detection module, and an antenna module. The bone screw body includes a cylinder. The spring structure, the detection module and the antenna module are respectively arranged in the accommodation portion of the column. The spring structure includes a body, a bearing part, a fixing part and at least one bending strain structure. One end of the body is connected to the bearing part, and the other end of the body is connected to the fixing part, and the fixing part is fixed in the cylinder. Each bending strain structure is respectively provided on the body. The body has an axial direction, and each bending strain structure has deformation in at least one direction different from the axial direction. The detection module includes at least one strain element and a sensing component.

22 Claims, 15 Drawing Sheets

(56) References Cited

U.S. PATENT DOCUMENTS

| | | | | |
|---|---|---|---|---|
| 11,707,224 B2 * | 7/2023 | Trabish | ................ | A61B 5/4585 |
| | | | | 600/595 |
| 11,723,594 B2 * | 8/2023 | Trabish | ................ | A61B 5/4585 |
| | | | | 607/60 |
| 2012/0163683 A1 * | 6/2012 | Wilson | ................. | A61B 5/4504 |
| | | | | 382/128 |
| 2020/0383796 A1 * | 12/2020 | Johannaber | ............ | A61B 34/25 |
| 2024/0122720 A1 * | 4/2024 | Glassman | ............ | A61B 5/4566 |
| 2025/0248742 A1 * | 8/2025 | Siby-Kurian | ...... | A61B 17/7032 |

FOREIGN PATENT DOCUMENTS

| | | | |
|---|---|---|---|
| CN | 107049233 A | 8/2017 |
| CN | 113423324 A | 9/2021 |
| CN | 117159237 A | 12/2023 |
| CN | 118102967 A | 5/2024 |
| CN | 118236176 A | 6/2024 |

OTHER PUBLICATIONS

Yokoya et al. "Effectiveness of measuring tension during archroscopic rotator cuff repair", Published in Journal of Experimental Orthopaedics:((2021) 8:21), Springer Open.
O'Connor et al. "Wireless Sensors for Smart Orthopedic Implants", Mar. 27, 2017, Journal of Bio-and Tribo-Corrosion.
Karipott et al. "An Embedded Wireless Temperature Sensor for Orthopedic Implants (https://www.semanticscholar.org/paper/An-Embedded-Wireless-Temperature-Sensor-for-Karipott-Veetil/4fa97b2fa92ad566490ab52c4386482a40f57a68)", Feb. 1, 2018, IEEE Senors Journal.

* cited by examiner

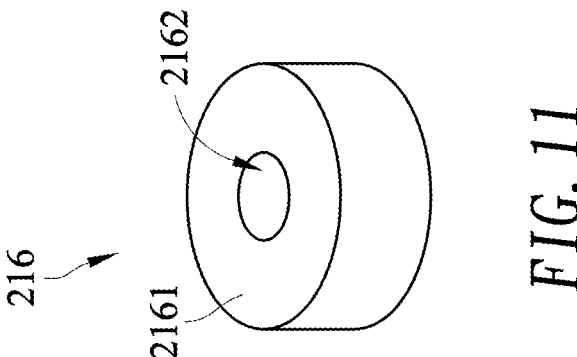
*FIG. 11*
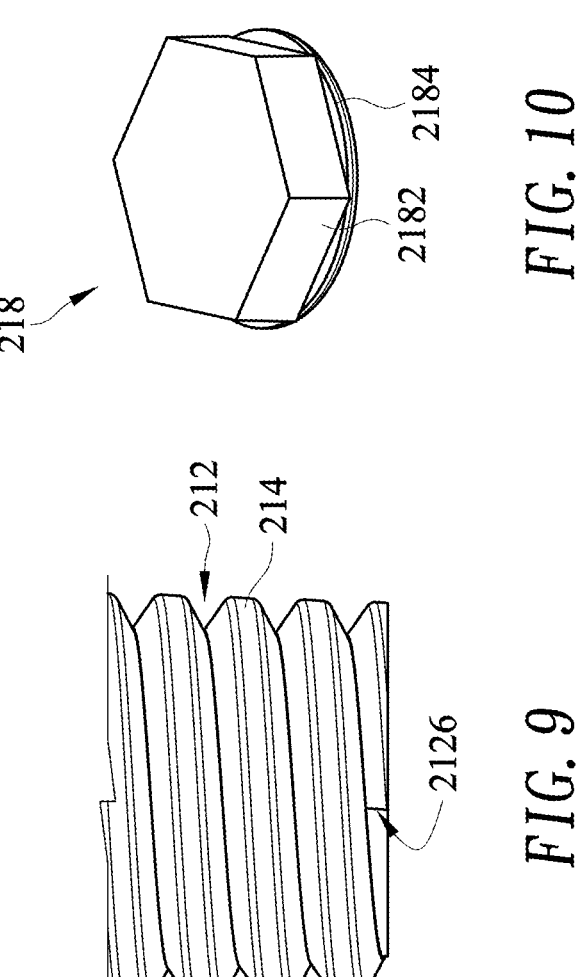
*FIG. 10*
*FIG. 9*

FORCE DETECTION BONE SCREW DEVICE

CROSS REFERENCE TO RELATED APPLICATION

This application claims the benefits of Taiwan application Serial No. 113150800, filed on Dec. 26, 2024, the disclosures of which are incorporated by references herein in its entirety.

TECHNICAL FIELD

The present disclosure relates to a bone screw device, and in particular to a force detection bone screw device.

BACKGROUND

The rotator cuff are a group of tendons located in the shoulder responsible for stabilizing the shoulder joint and assisting in shoulder movement. When these tendons are damaged or torn, it can result in shoulder pain and limited movement, especially in the elderly, and can even affect daily life. Rotator Cuff Repair surgery (RCR surgery) is a surgical operation used to repair injuries to the rotator cuff of the shoulder to reduce shoulder pain and restore function to the shoulder, allowing the patient to return to daily activities or sports.

In certain conventional technique, special fixation devices are commonly used in RCR to stabilize the tendon, such as rivets that penetrate deep into the bone and are secured by taping, thereby allowing the torn or damaged tendon tissue to reattach to the bone. After surgery, the patient usually needs physical therapy to restore strength and range of motion to the shoulder, which means post-surgical rehabilitation. Depending on the type of surgery and the extent of the injury, the recovery time can vary from a few months to a year, which makes the waiting time for healing too long, and overloading of the shoulder with rehabilitation can lead to re-tears. Tendon suture re-tears have the impact of leading to poorer clinical healing, accelerating joint degeneration, and making it more difficult to repair again.

In addition, during the surgical operation, the rivet implant may fail, causing re-tearing.

SUMMARY

The embodiments of the present disclosure provide a force detection bone screw device to solve or monitor the failure of rivet implants during surgery, and to prevent re-tearing caused by overloading during rehabilitation after surgery.

One embodiment of the present disclosure provides a force detection bone screw device for detecting the force of a suture. The force detection bone screw device includes a bone screw body, a spring structure, and a detection module, and an antenna module. The bone screw body includes a cylinder. The cylinder has an opening end and an insertion end opposite to each other. An accommodating portion in the cylinder is connected with the opening end. The spring structure is provided in the accommodation portion. The spring structure includes a body, a bearing part, a fixing part, and at least one bending strain structure. One end of the body is connected to the bearing part, and the other end of the body is connected to the fixing part. The fixing part is fixed inside the cylinder, and the fixing part is adjacent to the insertion end. One side of the bearing part is used to connect to the suture. Each bending strain structure is respectively arranged on the body. The body has an axial direction, and each bending strain structure has deformation in at least one direction different from the axial direction. The detection module is provided in the accommodating portion. The detection module includes at least one strain element and a sensing component. Each strain element is used to measure the stress of bending moment strain generated by the bending strain structure. One end of the sensing component is connected to the strain element. The antenna module is arranged in the accommodating portion, and the antenna module is connected to the sensing component.

A detailed description is given in the following embodiments with reference to the accompanying drawings, in order to make the disclosure more comprehensible.

BRIEF DESCRIPTION OF THE DRAWINGS

FIG. 9 is a partial three-dimensional schematic diagram of the bone screw body according to FIG. 8.

FIG. 10 is a three-dimensional schematic diagram of an embodiment of the bottom cover according to FIG. 8.

FIG. 11 is a three-dimensional schematic diagram of an embodiment of the plug cover according to FIG. 8.

DETAILED DESCRIPTION

The following embodiments are set forth in detail with accompanying drawings, but the embodiments provided are not intended to limit the scope of the disclosure. In addition, the drawings are for illustrative purposes only and are not drawn to original size. To facilitate understanding, the same components will be identified with the same symbols in the following description.

The following embodiments are set forth in detail with accompanying drawings, but the embodiments provided are not intended to limit the scope of the disclosure. In addition, the drawings are for illustrative purposes only and are not drawn to original size. To facilitate understanding, the same components will be identified with the same symbols in the following description.

The terms "including", "comprising", "having", etc. mentioned in the disclosure are open terms, which means "including but not limited to".

In the description of the various embodiments, when describing the elements by the terms "first," "second," "third," "fourth," and the like, it is used only to distinguish these components from one another and does not limit the order or importance of these components.

In the description of various embodiments, the term "coupled" or "connected" may refer to two or more elements being in direct physical or electrical contact with each other, or in indirect physical or electrical contact with each other, and the term "coupled" or "connected" may also refer to the two or more elements being operated or acted upon by each other.

In the description of various embodiments, the term "module" refers to a hardware module, i.e., a hardware component that occupies space. In other embodiments, the term "module" may also refer to a hardware module plus a software module, i.e., the "module" not only has hardware components, but also has software programs.

Figure 1:
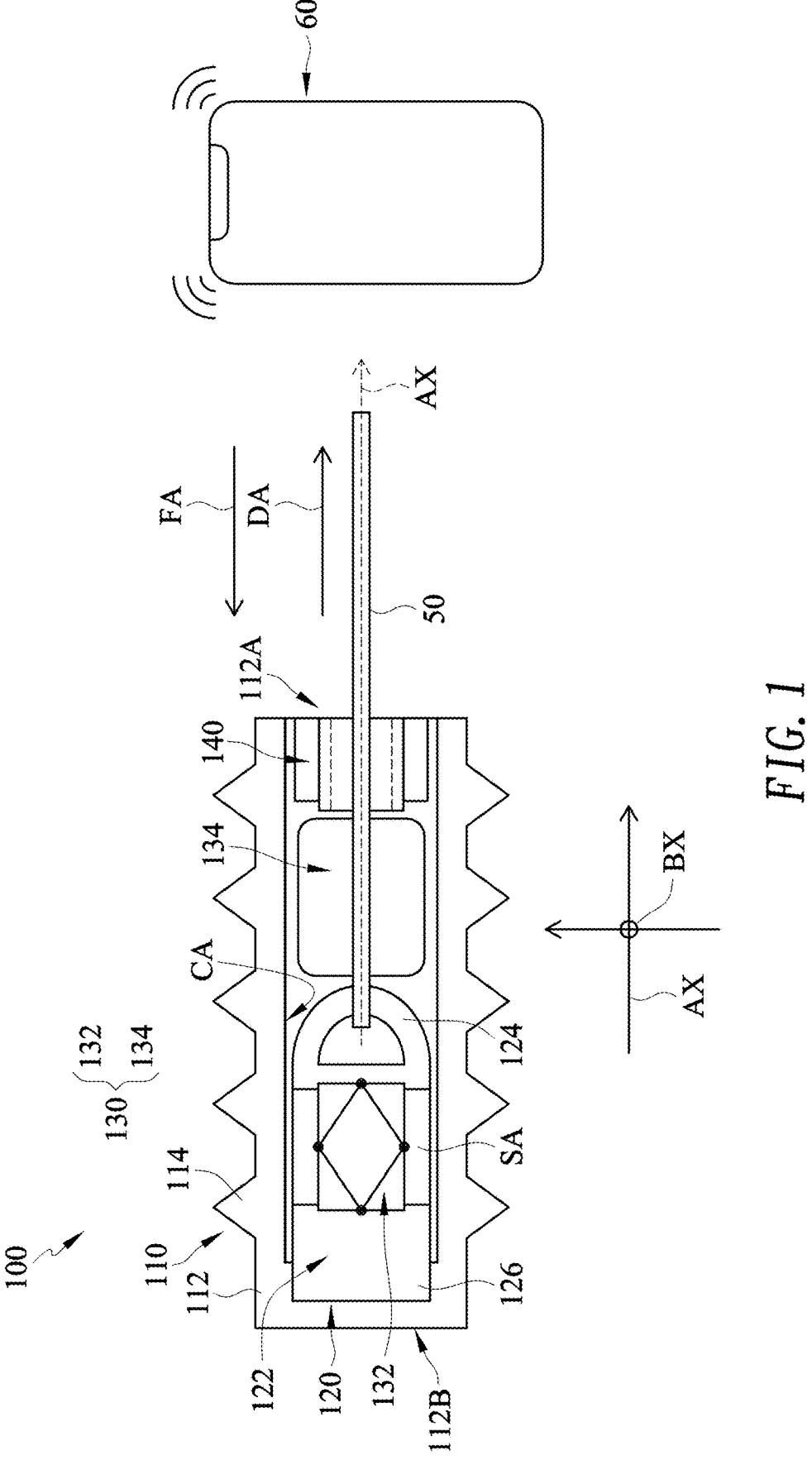
FIG. 1 is a schematic diagram of a force detection bone screw device according to the present disclosure.

FIG. 1 is a schematic diagram of a force detection bone screw device according to the present disclosure. Please refer to FIG. 1. The force detection bone screw device 100 of the present disclosure is used to detect the force of a suture 50. The force can be tension, or be used to detect the force change or tension change of the suture 50. The force detection bone screw device 100 may be, for example, a suture anchor, and inserted into the human shoulder to serve as a fixation device for RCR surgery to stabilize tendons. In other embodiments, the force detection bone screw device 100 can be applied to other human orthopedic portions according to the situation. The size of the force detection bone screw device 100 can be, for example, as follows: the outer diameter of the force detection bone screw device 100 ranges from 2 mm to 30 mm, and the length of the force detection bone screw device 100 ranges from 5 mm to 500 mm. The size of the bone screw body 110 can be, for example, as follows: the outer diameter of the bone screw body 110 ranges from 2 mm to 30 mm, and the length of the bone screw body 110 ranges from 5 mm to 500 mm. The size of the spring structure 120 can be, for example, as follows: the diameter or width of the spring structure 120 ranges from 4 mm to 18 mm, and the thickness of the spring structure 120 ranges from 0 mm to 10 mm.

The force detection bone screw device 100 of the present disclosure includes a bone screw body 110, a spring structure 120, a detection module 130, and an antenna module 140. The spring structure 120, the detection module 130 and the antenna module 140 are respectively disposed in an accommodating portion CA within the bone screw body 110.

The shape of the bone screw body 110 of the present disclosure can be adjusted based on the actual application situation. The bone screw body 110 includes a cylinder 112 and a plurality of threads 114 which can be disposed optionally. These threads 114 are protruded and provided from the outer surface of the cylinder 112. In other embodiments, the bone screw body 110 may be a three-dimensional structure without threads on its outer surface.

The cylinder 112 has an opening end 112A and an insertion end 112B opposite to each other. The opening end 112A is connected within the accommodating portion CA. The insertion end 112B is the end of the bone screw body 110 inserted into the human bone, and the opening end 112A can be pulled out from the suture 50. Taking the suture anchor as an example. During the use in orthopedic or joint surgeries, one end of the suture 50 can be connected to human tendons or bones. These bone screw body 110 can fix the suture 50 firmly to the bones or other tissues, so as to help repairing torn ligaments, tendons, or other tissues.

The spring structure 120 of the present disclosure refers to a structure for withstanding and sharing external loads or pressures. The spring structure 120 includes a body 122, a bearing part 124, a fixing part 126, and a bending strain structure SA. That is, the spring structure 120 is a structure for measuring the deformation of the force to be applied by the strain gauge. One end of the body 122 is connected to the bearing part 124, and the other end of the body 122 is connected to the fixing part 126. The bending strain structure SA is a structure for structural strain (deformation) and response caused by bending moment action. The bending strain structure SA is provided on the body 122.

The body 122 of the present disclosure has an axial direction AX, and the axial direction AX can be parallel to the length direction of the body 122. The fixing part 126 is fixed at the bottom inside the cylinder 112. That is, the fixing part 126 is adjacent to the insertion end 112B, so that the fixing part 126 serves as a fixing end of the spring structure 120. In addition, one side of the bearing part 124 is connected to the suture 50, and the suture 50 can be stretched upwardly along the axial direction AX. In other words, the bearing part 124 serves as one of the movable ends of the spring structure 120.

When the suture 50 is pulled up with an external force acting on the spring structure 120, a moment of force (bending moment) will be generated to bend the bending strain structure SA. The bending strain structure SA has a deformation in at least one direction different from the axial direction AX. For example, different deformations will occur at different locations inside the bending strain structure SA, and these deformations are strains.

As such, when the suture 50 is pulled up along the axial direction AX, the suture 50 drives the bearing part 124 and its connected body 122 to move along the axial direction AX. Since the fixing part 126 does not move, when the body 122 moves along the axial direction AX, the bending strain structure SA will deform in at least two directions due to the movement of the body 122.

Taking FIG. 1 as an example, the bending strain structure SA not only has deformation along the axial direction AX, but also can deform along the vertical direction BX perpendicular to the axial direction AX, thus having deformation in two directions.

The detection module 130 of the present disclosure includes a strain element 132 and a sensing component 134. One end of the sensing component 134 is connected to the strain element 132, and the other end of the sensing component 134 is connected to the antenna module 140 to constitute a sensing and wireless structure.

The strain element 132 is used to measure the stress generated by the bending strain structure SA in the body 122. The strain element 132 is disposed at a corresponding position of the bending strain structure SA in the body 122. The strain element 132 is a strain gauge or measures force through a piezoelectric material structure. The strain gauge is made of conductive material. The strain gauge is used to measure the stresses that cause bending deformation due to the forces applied to the bending strain structure SA. The piezoelectric material (such as some crystals or ceramics) has a piezoelectric effect. When a piezoelectric material is subjected to a bending moment stress generated by the bending strain structure SA, a voltage will be generated on its surface. The magnitude of the voltage is proportional to the force applied, and it can be used to measure the magnitude of force or pressure.

When the suture 50 drives the bearing part 124 and its connected body 122 to move along the axial direction AX and exerts force on the spring structure 120, the bending strain structure SA deforms, causing the resistance value of the strain element 132 to change. The change of the resistor is converted into an electrical signal and transmitted to the sensing component 134 to form a voltage change. Afterwards, the sensing component 134 measures and uses it to calculate the applied force as a force data DA.

Because the force detection bone screw device 100 is a smart sensing implant with miniaturized size, the size of the spring structure 120 is also a small size. If only the small strain of the axial force on the axial direction AX is provided when the spring structure 120 is stretched, the force that can be converted in response to the signal is small, resulting in a difficult detection and a weak signal. However, in addition to the deformation along the axial direction AX, the bending strain structure SA of the present disclosure can also deform along the vertical direction BX perpendicular to the axial direction AX. Based on the foregoing, by having the structural characteristics of the bending strain structure SA, the small strain of the axial force of the spring structure 120 along the axial direction AX can be converted into a larger bending moment strain. Accordingly, the corresponding shape strains in the axial direction AX and the vertical direction BX can be provided, allowing the detection module 130 to generate a signal corresponding to the force data DA that is large enough and linear, so as to improve detection quality and meet the needs of miniaturization of smart sensing implants.

In one application embodiment, during exercise or rehabilitation process, the suture 50 moves during the movement of the joint, causing the tension of the suture 50 to change. As such, the suture 50 applies force to the spring structure 120, allowing the spring structure 120 to have displacement and deformation. Through the structural characteristics of the bending strain structure SA, the detection module 130 calculates the applied force as the force data DA according to the converted voltage change value of the bending moment strain corresponding to the bending strain structure SA. Accordingly, it can be evaluated whether the data DA exceeds the load, in order to avoid the probability of tendon re-tearing after suturing, monitor the degree of recovery at this time, and achieve the purpose of accelerating healing.

Furthermore, during the surgical operation, the present disclosure can be used as a monitoring mechanism to monitor the rivet implant during surgery, to avoid or reduce the occurrence of rivet implant failure.

In one embodiment, the material of the spring structure 120 and the bone screw body 110 as shown in FIG. 1 can be made of polyetheretherketone (PEEK), which is a PEEK structure. PEEK is a thermoplastic with high-temperature resistance, mechanical strength, chemical stability, electrical insulation, and biocompatibility. PEEK can be used at high temperatures for a long time, and it can withstand higher temperatures in a short period of time. PEEK has high tensile strength, hardness, and wear resistance, and is suitable for applications requiring high strength. PEEK has strong corrosion resistance to most chemical substances. PEEK has better electrical insulation properties, and thus it can be used in the electronic modules and communication modules used in the present disclosure. PEEK has been widely used in the medical field, especially in the smart sensing implants. PEEK is biocompatible and safe for use in the human body.

In addition, the bone screw body 110 is made of PEEK material, instead of metal material, to avoid shielding effect for affecting the operation of the antenna module 140.

In other embodiments, the bone screw body 110 and the spring structure 120 can also be made of non-magnetic metals, and be a non-magnetic metal structure, such as stainless steel or titanium alloy with anti-magnetic conductivity function.

Figure 2:
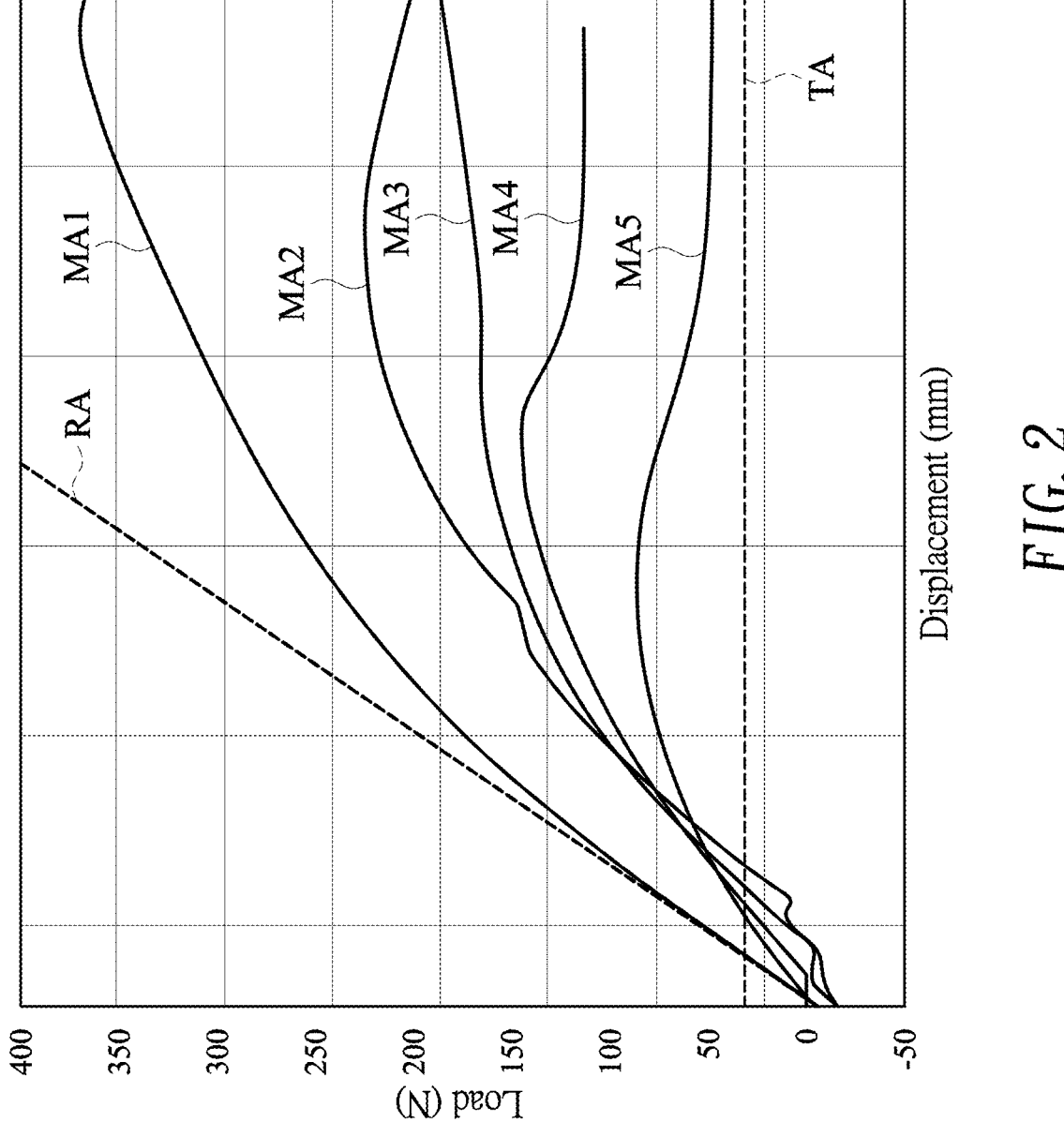
FIG. 2 is a schematic diagram of comparative data for material selection of the spring structure according to the present disclosure.

FIG. 2 is a schematic diagram of comparative data for material selection of the spring structure according to the present disclosure. Please refer to FIG. 2. The horizontal axis of FIG. 2 is displacement with unit of millimeters (mm). The vertical axis of FIG. 2 is load with unit of Newton (N). FIG. 2 has a theoretical curve RA in which five materials were used as spring structure as experiments to obtain the first material curve MA1, the second material curve MA2, the third material curve MA3, the fourth material curve MA4, and the fifth material curve MA5. The first material curve MA1 is the data obtained by using PEEK as the material of the spring structure. The second material curve MA2 is the data obtained by using 4K_3DP (high-strength 3D printing engineering resin) as the material of the spring structure. The third material curve MA3 is the data obtained by using 2K_3DP (low-strength 3D printing engineering resin) as the material of the spring structure. The fourth material curve MA4 is the data obtained by using plastic (PP, also known as polypropylene) as the material of the spring structure. The fifth material curve MA5 is the data obtained by using HDPE (High-Density Polyethylene) as the material of the spring structure.

As shown in FIG. 2, compared with the second material curve MA2, the third material curve MA3, the fourth material curve MA4 and the fifth material curve MA5 exhibiting a fast decline in the curve trend, the first material curve MA1 under the tension of the load 100N can be close to the theoretical curve RA, which proves that the use of PEEK material in the disclosed spring structure 120 exhibits a wide range of tension detection. Moreover, under the specific tension value TA of 30N, the first material curve MA1 is linear, which indicates that the displacement of the spring structure 120 using PEEK material can be proportional to the load data of the tension. In one embodiment, the spring structure 120 of PEEK material is used, and the tension detection range of the force detection bone screw device 100 is between 0 to 3 Kgf, where 3 Kgf is about 30 Newtons.

Moreover, in association with the structural characteristics of the bending strain structure SA, the small strain of the axial force caused by the tension of the load spring structure 120 along the axial direction AX can be converted into a larger bending moment strain. Accordingly, the detection module 130 generates a signal corresponding to the force data DA that is large enough and linear to greatly improve the detection quality.

The antenna module 140 of the present disclosure can have wireless communication (such as Wi-Fi, Bluetooth, 4G/5G) function. The power data DA can be transmitted to an external hardware device 60 through the antenna module 140, and the status of force data DA can be calculated through the hardware device 60. The hardware device 60 can be, for example, a handheld electronic device or a cloud device.

In an optional embodiment, the hardware device 60 can transmit energy FA to the antenna module 140 in the force detection bone screw device 100. The energy FA is, for example, electricity. Based on the foregoing, it can be seen that the force detection bone screw device is charged through the antenna module 140 so as to provide a battery-free device. Of course, in other embodiments, the force detection bone screw device 100 can be charged in other ways.

Figure 3:
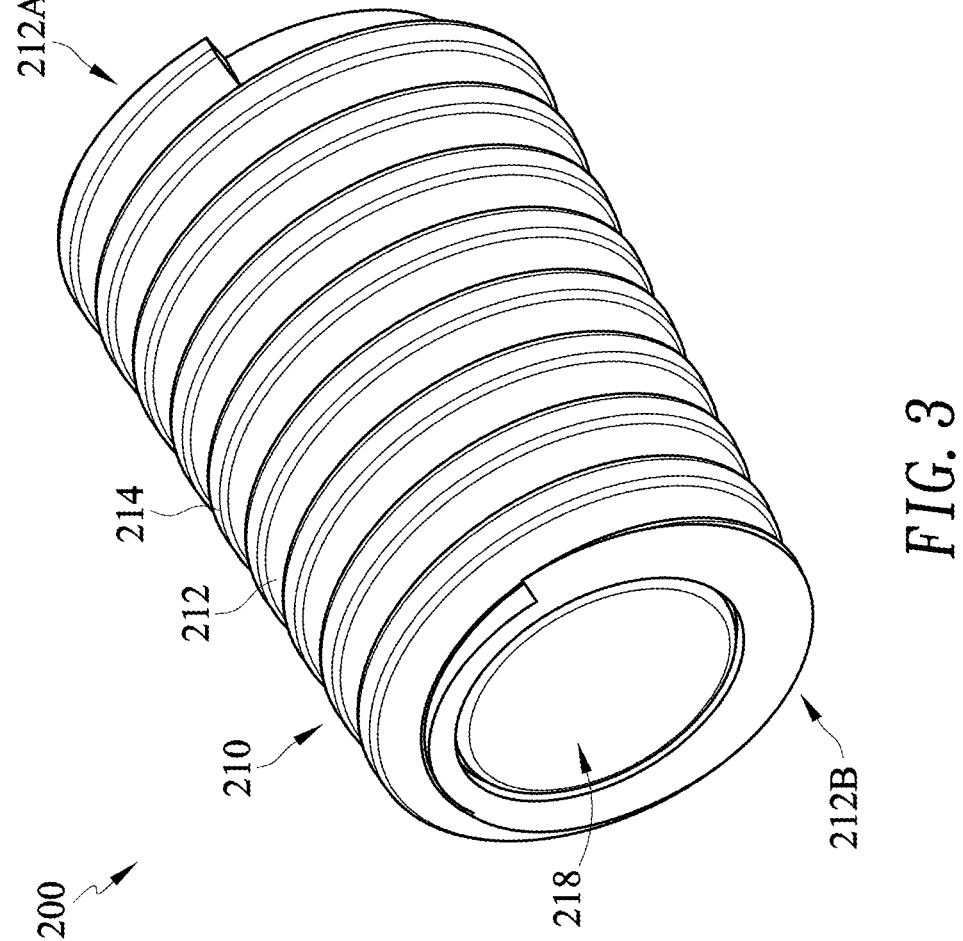
FIG. 3 is a three-dimensional schematic diagram of an embodiment of a force detection bone screw device according to the present disclosure.
Figure 4:
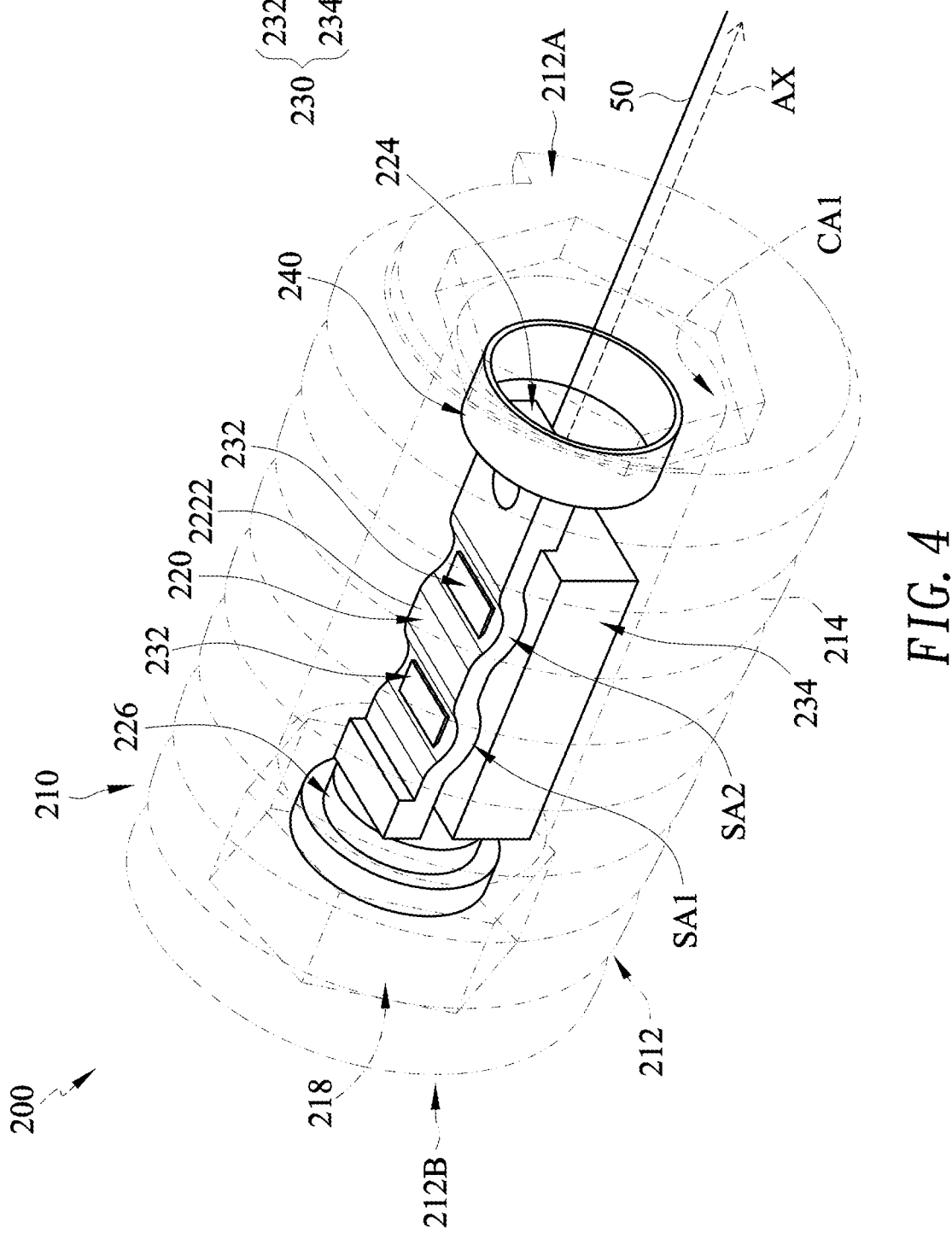
FIG. 4 is a three-dimensional schematic diagram of the interior according to the force detection bone screw device of FIG. 3.
Figure 5:
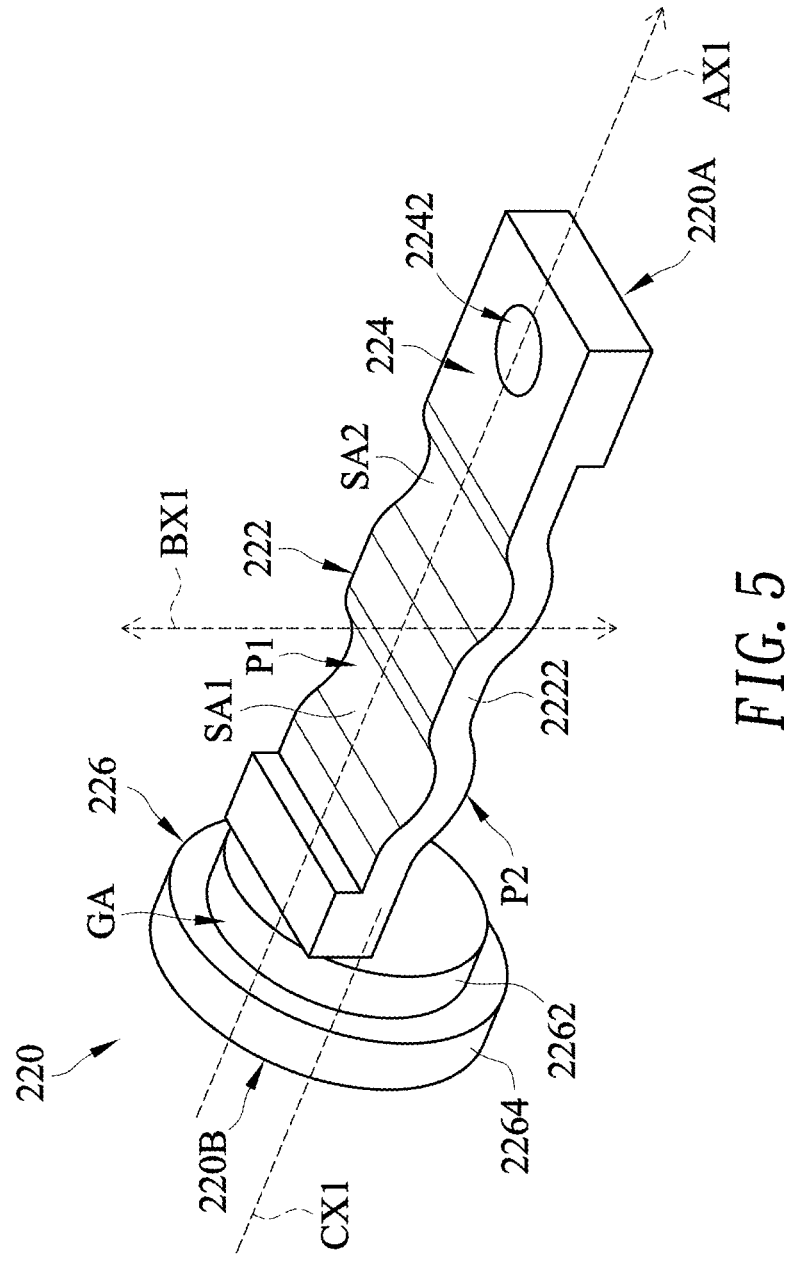
FIG. 5 is a three-dimensional schematic diagram of an embodiment of a spring structure according to the present disclosure.

FIG. 3 is a three-dimensional schematic diagram of an embodiment of a force detection bone screw device according to the present disclosure. FIG. 4 is a three-dimensional schematic diagram of the interior according to the force detection bone screw device of FIG. 3. FIG. 5 is a three-dimensional schematic diagram of an embodiment of a spring structure according to the present disclosure. Please refer to FIGS. 3, 4 and 5 to illustrate an embodiment of the application structure. The force detection bone screw device 200 of the present disclosure includes a bone screw body 210, a spring structure 220, a detection module 230, and an antenna module 240.

The bone screw body 210 includes a cylinder 212, a plurality of threads 214 and a bottom cover 218. The threads 214 are respectively protruded and arranged from the outer surface of the cylinder 212. The bottom cover 218 is disposed and closed on the bottom of the cylinder 212. The column 212 can be a cylindrical structure or any other three-dimensional structure. The threads 214 can be screwed in by the user, or the configuration of the threads 214 can be changed based on actual conditions. The cylinder 212 has an opening end 212A and an insertion end 212B opposite to each other. One side of the bottom cover 218 is the insertion end 212B. The opening end 212A is connected within the accommodating portion CA1. The insertion end 212B is the end of the bone screw body 210 that is inserted into the human bone, and the opening end 212A is for the suture 50 to be pulled out.

The spring structure 220, the detection module 230 and the antenna module 240 are respectively provided in the accommodating portion CA1 within the bone screw body 110. The spring structure 220 of the present disclosure includes a body 222, a bearing part 224, a fixing part 226, and two bending strain structures SA1 and SA2. That is, the spring structure 220 is a structure that is used to measure the deformation of the force to be applied by the strain gauge. One end of the body 222 is connected to the bearing part 224, and the other end of the body 222 is connected to the fixing part 226. The antenna module 240 may be a hollow ring-shaped structure, and it is disposed outside the fixing part 226.

The body 222 of the present disclosure can be a plate body having an axial direction AX1. The axial direction AX1 of the body 222 can be parallel to the length direction of the body 222. The two bending strain structures SA1 and SA2 can serve as structures for structural strain (deformation) and response caused by bending moment action, and they are respectively provided at different positions of the body 222.

The detection module 230 is connected to the antenna module 240. The detection module 230 includes two strain elements 232 and a sensing component 234. The two strain elements 232 are respectively provided in the bending strain structures SA1 and SA2. In the embodiment, the body 222 in the spring structure 220 and the bearing part 224 connected thereto are connected to the fixing part 226 in an eccentric setup manner. In other words, the body 222 and the bearing part 224 connected thereto are offset from a center axes CX1 or a center position of the fixing part 226.

Since the body 222 and the bearing part 224 connected thereto are eccentric setup, there is still an accommodating space at the lower end side of the body 222. The sensing component 234 can be disposed at the lower end side of the body 222. As such, the sensing component 234 can be positioned between the fixing part 226 and the antenna module 240, thereby reducing the accommodating space of the accommodating portion CA1 in the bone screw body 210. In other embodiments not shown, the body and the bearing part connected thereto may be located at the central axis or the center position of the fixing part according to the actual structural configuration or requirements, and the sensing component can be connected to one side of the bearing part.

Taking FIG. 5 as an example, the spring structure 220 has a movable end 220A and a fixing end 220B opposite to each other. The fixing part 226 is fixed at the bottom inside the cylinder 212, so that the fixing part 226 serves as a fixing end 220B of the spring structure 120. The bearing part 224 has a hole 2242, and the hole 2242 can be connected to the suture 50, so that the suture 50 can be stretched along the axial direction AX1.

The fixing part 226 includes an engaging element 2262 and a bottom element 2264. The engaging element 2262 is connected between the body 222 and the bottom element 2264. The other side of the bottom element 2264 is the fixing end 220B of the spring structure 220. The bottom cover 218 is disposed and closed at the bottom of the cylinder 212, and the bottom element 2264 is disposed on one side of the bottom cover 218. In one embodiment, the bottom element 2264 can be supported against the bottom cover 218.

The engaging element 2262 and the bottom element 2264 of the present disclosure are respectively a cylinder. The difference lies in that the size of the engaging element 2262 is smaller than the size of the bottom element 2264, so that the engaging element 2262 has an engaging structure GA. The engaging structure GA is used to bond within the cylinder 212 and to stabilize the fixing end 220B of the spring structure 220 within the bone screw body 110.

The two bending strain structures SA1 and SA2 have a deformation amount respectively in at least one direction different from the axial direction AX1. Taking FIG. 5 as an example, the two bending strain structures SA1 and SA2 are actually a concave structure or a curved structure of the body 222. The body 222 has a planar portion 2222. The bending strain structures SA1 and SA2 are recessed structures or bent structures that are recessed or bent from the surface of the planar portion 2222. Alternatively, the bending strain structures SA1 and SA2 are structures that are not parallel to the surface of the planar portion 2222. As such, in addition to the deformation along the axial direction AX1, the two bending strain structures SA1 and SA2 can also deform along the vertical direction BX1 perpendicular to the axial direction AX1. The vertical direction BX1 is the direction perpendicular to the body 222, for example, the normal direction of the body 222. By utilizing the structural configuration, the two bending strain structures SA1 and SA2 are structures for structural strain (deformation) and response caused by the bending moment action.

Figure 6:
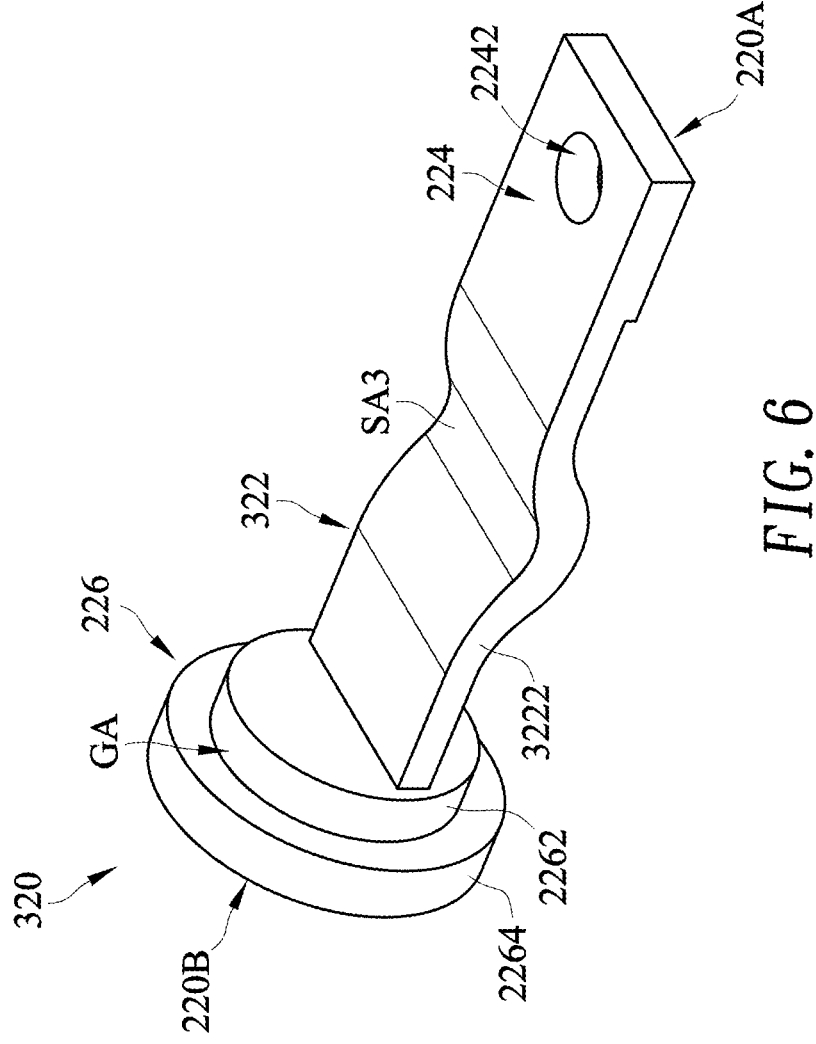
FIG. 6 is a three-dimensional schematic diagram of another embodiment of the spring structure according to the present disclosure.

In other embodiments, the difference between the spring structure 320 shown in FIG. 6 and the spring structure 220 shown in FIG. 5 lies in that the number of the bending strain structure SA3 is one. In other words, the bending strain structure SA3 in FIG. 6 is a bend or a recessed position of the planar portion 3222 in the body 322.

Figure 7:
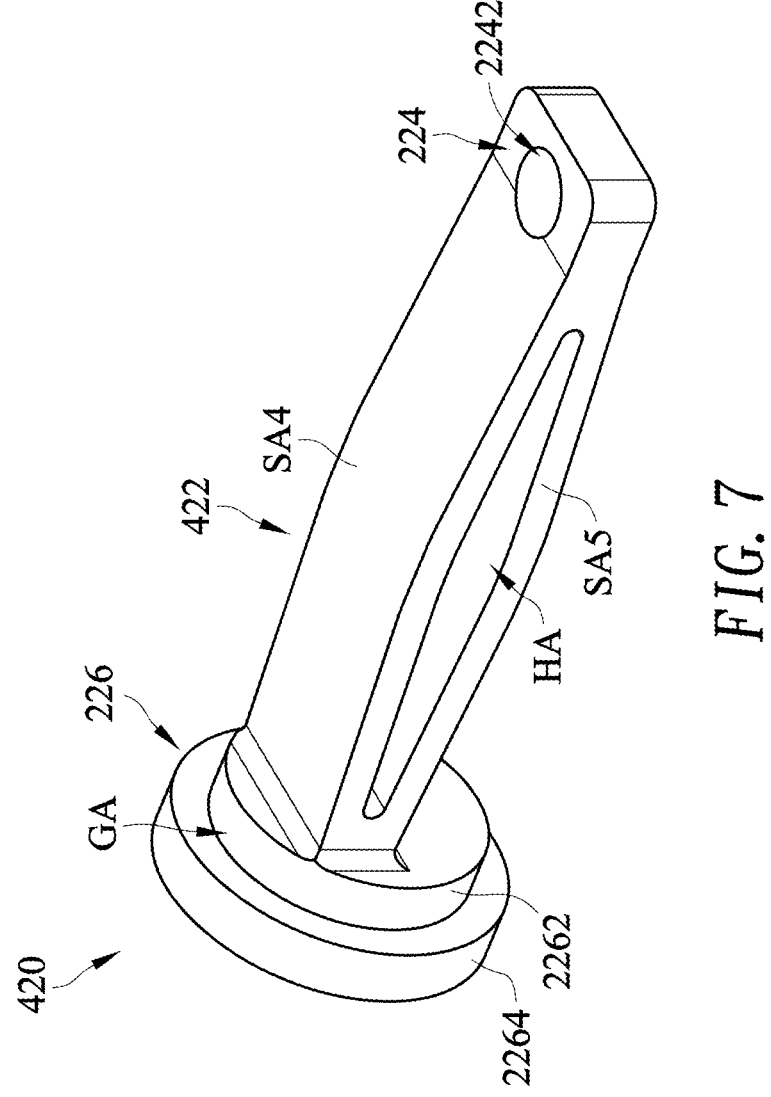
FIG. 7 is a three-dimensional schematic diagram of another embodiment of the spring structure according to the present disclosure.

In other structural embodiments, the difference among the spring structure 420 shown in FIG. 7, the spring structure 220 shown in FIG. 5 and the spring structure 320 shown in FIG. 6 is that the accommodating portion HA is provided at the center of the body 422 to form an upper bending strain structure SA4 and a lower bending strain structure SA5. That is, the accommodating portion HA is an accommodation space between the bending strain structure SA4 and the bending strain structure SA5. The bending strain structure SA4 and the bending strain structure SA5 are curved structures compared to the bearing part 224.

As can be seen from FIGS. 4 to 7, the bending strain structures SA1, SA2, SA3, SA4, and SA5 in the embodiment are three-dimensional arc (nonlinear) configurations of the spring structures 220, 320, and 420 and can provide stress concentration areas. Additionally, it can partially generate the shape structure of the stress concentration area. Through the shape structure partially generating the stress concentration area, the small strains of the axial force of the spring structure 220, 320, 420 being stretched along the axial direction AX can be converted into larger bending moment strains.

As shown in FIG. 5, the bending strain structure SA1 has a concave surface P1 and a convex surface P2 opposite to each other, and the strain element 232 as shown in FIG. 4 can be disposed on the concave surface P1. In other embodiments, the strain element can also be disposed on the convex surface, so that the strain element can be disposed at one of the positions of the concave surface P1 and the convex surface P2. Similarly, the method of arranging the strain elements 232 on the concave surface P1 and the convex surface P2 of the bending strain structure SA1 can be applied to the bending strain structure SA2 and the bending strain structure SA3 in FIG. 6.

As shown in FIG. 7, the strain element 232 in FIG. 4 can be disposed within the accommodating portion HA, and the deformation of the bending strain structures SA4 and SA5 can also be detected. Alternatively, the strain element 232 as shown in FIG. 4 can be disposed on the outer surfaces of the bending strain structures SA4 and SA5.

Figure 8:
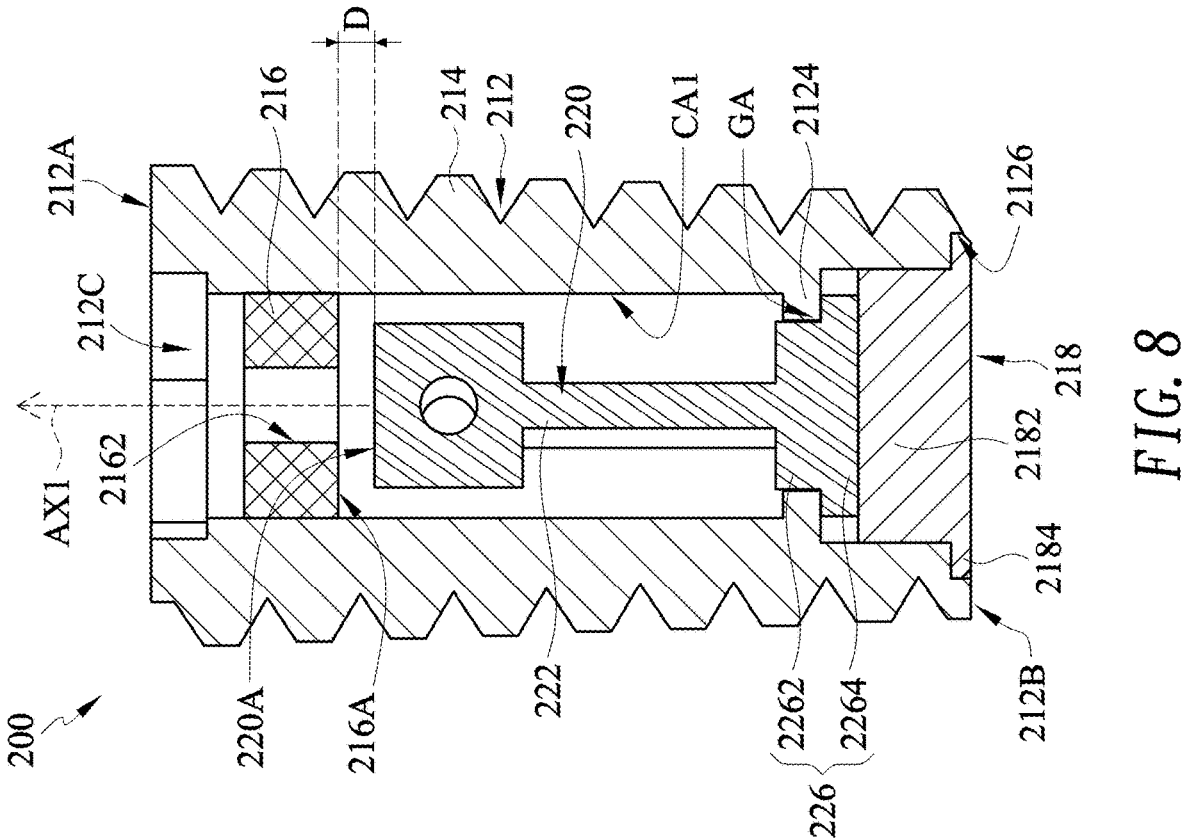
FIG. 8 is a schematic cross-sectional view of another embodiment of the force detection bone screw device according to the present disclosure.

FIG. 8 is a schematic cross-sectional view of another embodiment of the force detection bone screw device according to the present disclosure. FIG. 9 is a partial three-dimensional schematic diagram of the bone screw body according to FIG. 8. FIG. 10 is a three-dimensional schematic diagram of an embodiment of the bottom cover according to FIG. 8. FIG. 11 is a three-dimensional schematic diagram of an embodiment of the plug cover according to FIG. 8. Please refer to FIGS. 8 to 11. The force detection bone screw device 200 in FIG. 8 can be a schematic cross-sectional view of the force detection bone screw device 200 in FIG. 3. A protruding structure 2124 is disposed inside the cylinder 212. The protruding structure 2124 is a flange on the inner surface of the cylinder 212 and is located within the accommodating portion CA1. The spring structure 220 can be inserted into the cylinder 212 from the insertion end 212B until the engaging structure GA rests against the protruding structure 2124. Accordingly, the protruding structure 2124 is locked in the engaging structure GA to fix the location of the spring structure 220. In other embodiments not shown, the spring structure 220 and the cylinder 212 may have other mechanisms such as form-fitting (e.g., concave-convex bonding) mechanisms for mutual bonding, all of which are similar and equal in effect to the embodiment.

Afterwards, the bottom cover 218 is disposed and closed on the bottom of the cylinder 212, and the bottom element 2264 can be supported against the bottom cover 218. In one embodiment, a card groove structure 2126 is provided at the bottom of the cylinder 212, and the card groove structure 2126 is a gap at the bottom of the cylinder 212. The bottom cover 218 includes an anti-rotation structure 2182 and a cover body 2184. The anti-rotation structure 2182 is connected to the cover body 2184. The bottom of the cover body 2184 is flat. The anti-rotation structure 2182 is screwed into the cylinder 212 by screwing in. Furthermore, the side edge of the cover body 2184 is combined with the card groove structure 2126, so that the bottom cover 218 is combined with the cylinder 212.

In addition, the shape and structure design of the anti-rotation structure 2182 of the bottom cover 218 can prevent it from spinning and falling off. The shape of the anti-rotation structure 2182 is a hexagonal structure as shown in FIG. 10. In other embodiments not shown, the anti-rotation structure can be a polygonal or other shaped structure, and any shape structure that can prevent rotation is within the scope of the present disclosure.

On the other hand, a turn-in structure 212C is provided within the cylinder 212 near the opening end 212A. The turn-in structure 212C is, for example, an inner hexagonal structure within the cylinder 212, which is the position for the user to use tools (such as a hex wrench) to combine with the bone screw body 210. In other embodiments, the shape and structural configuration of the turn-in structure 212C can be adjusted according to the tool. In other words, the shape and structural configuration of the turn-in structure 212C can be different shapes. The ability to rotate into the bone by rotating the tool into the turn-in structure 212C during surgery is within the scope of this disclosure.

As shown in FIGS. 8 and 11, the bone screw body 210 also includes a plug cover 216, which is a sunken plug cover. The plug cover 216 is disposed below the turn-in structure 212C to avoid anti-rotation and plugging. In addition, the plug cover 216 is located at the upper position of the spring structure 220, so that the plug cover 216 is disposed between the turn-in structure 212C and the spring structure 220. In one embodiment, there is a distance D between the bottom portion 216A of the plug cover 216 and one side of the bearing part 224 in the spring structure 220. Accordingly, when the spring structure 220 is stretched by the suture and is displaced, it will not touch the plug cover 216.

The plug cover 216 includes a plug cylinder 2161 and a suture through hole 2162. The plug cylinder 2161 is, for example, a cylinder. The suture through hole 2162 is perforated in the center of the plug cylinder 2161 for the suture to pass out from the side of the spring structure 220 outside the bone screw body 210. In one embodiment, the antenna module 240 as shown in FIG. 4 can be combined with the plug cover 216, or the antenna module 240 can be connected to one side of the plug cover 216, all of which are similar and equal in effect to the embodiment. In one embodiment, the axial direction AX1 of the spring structure 220 passes through the suture through hole 2162 and has a positioning function.

Figure 12:
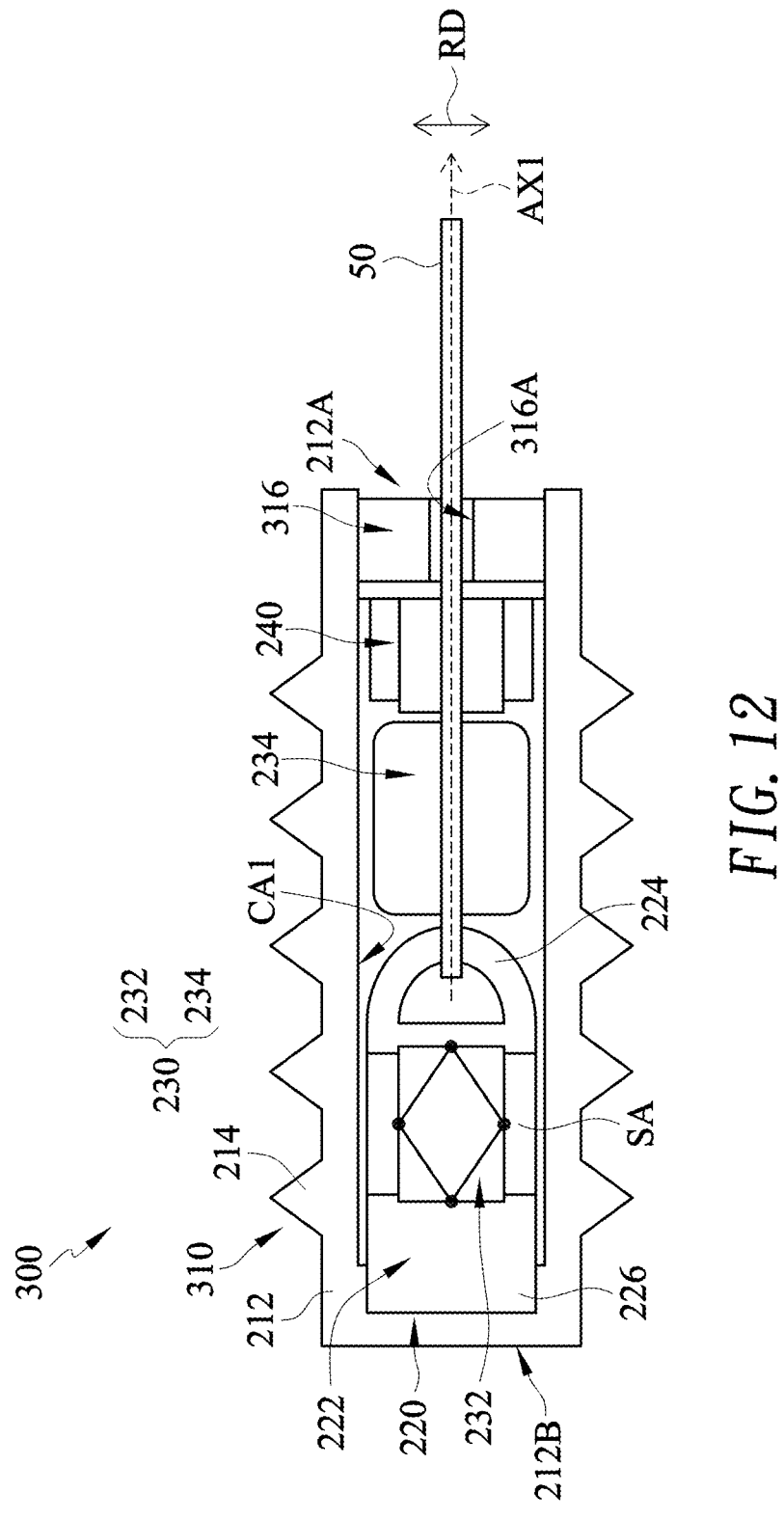
FIG. 12 is a schematic diagram of another embodiment of a force detection bone screw device according to the present disclosure.
Figure 13:
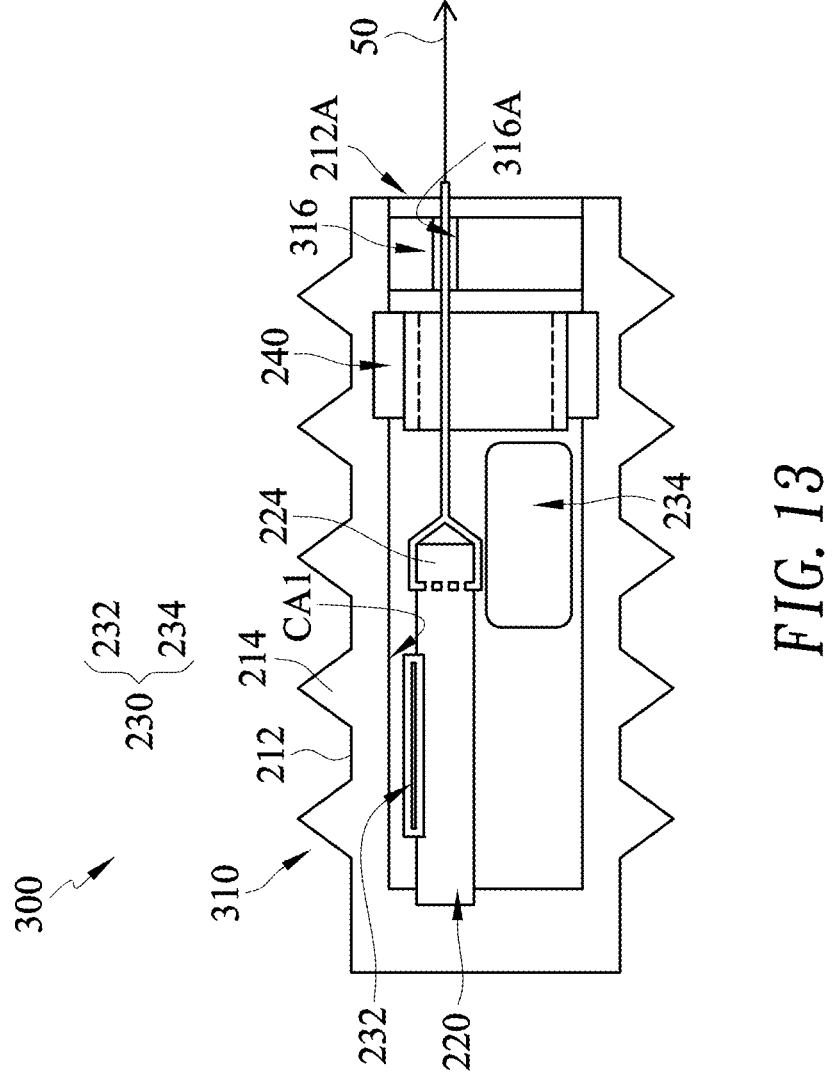
FIG. 13 is a schematic side view of another embodiment of the force detection bone screw device according to the present disclosure.

FIG. 12 is a schematic diagram of another embodiment of a force detection bone screw device according to the present disclosure. FIG. 13 is a schematic side view of another embodiment of the force detection bone screw device according to the present disclosure. Please refer to FIGS. 12 to 13. The difference between the force detection bone screw device 300 of the present disclosure and the force detection bone screw device 200 of FIG. 8 lies in that the plug cover 316 in the bone screw body 310 is provided with a positioning pin hole 316A. The hole diameter of the positioning pin hole 316A can be smaller than the hole diameter of the suture through hole 2162 as shown in FIG. 8, and the hole diameter of the positioning pin hole 316A is larger than the size of the suture 50 for the suture 50 to pass through.

The positioning pin hole 316A of the present disclosure has a smaller hole diameter and can limit the movement of the suture 50 in the radial direction RD within the positioning pin hole 316A. In one embodiment, as shown in FIG. 12 and FIG. 13, the axial direction AX1 of the spring structure 220 can pass through the positioning pin hole 316A. The structural arrangement of the positioning pin hole 316A and the positional conditions of the positioning pin hole 316A and the spring structure 220 enable the suture 50 to exert force along the axial direction AX1 of the spring structure 220, limiting the tension of the suture 50 on the axial direction AX1 of the spring structure 220. That is, the position of the positioning pin hole 316A enables the force application conditions to be oriented and fixed, and solves the problem of non-axial component force. It should be noted that, in one embodiment, the suture through hole 2162 of the plug cover 216 in FIG. 11 can also adopt the position conditions of this embodiment to have the positioning function of the positioning pin hole 316A.

Figures 14, 15, 16:
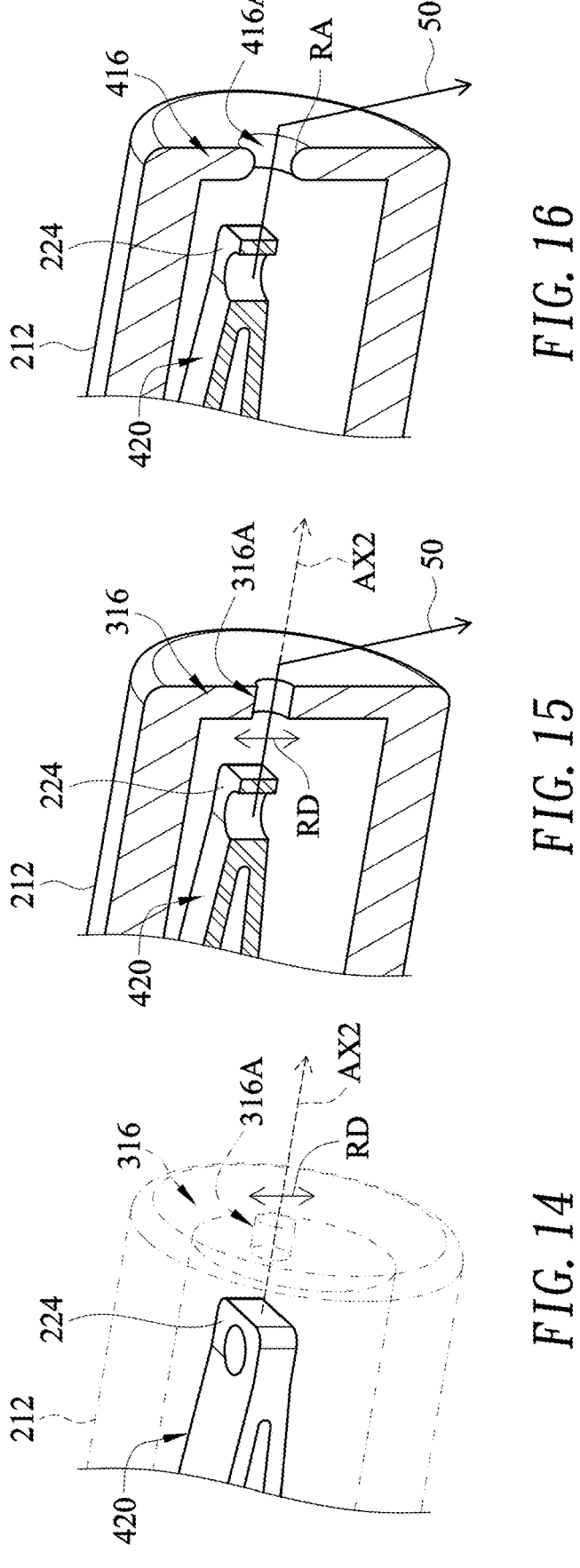
FIG. 14 is a three-dimensional schematic diagram of an embodiment of a spring structure and a positioning pin hole according to the present disclosure.
FIG. 15 is a schematic cross-sectional view of an embodiment of the spring structure and positioning pin hole according to FIG. 14.
FIG. 16 is a schematic cross-sectional view of another embodiment of the spring structure and positioning pin hole according to the present disclosure.

FIG. 14 is a three-dimensional schematic diagram of an embodiment of the spring structure and the positioning pin hole according to the present disclosure. FIG. 15 is a schematic cross-sectional view of an embodiment of the spring structure and the positioning pin hole according to FIG. 14. Please refer to FIGS. 14 and 15. In terms of the setting height direction, for example, if the spring structure 420 in FIG. 7 is used, its setting height position will be the same as the setting height position of the positioning pin hole 316A. Accordingly, the axial direction AX2 of the spring structure 420 will pass through the positioning pin hole 316A to achieve the effect of limiting the tension of the suture 50 in the axial direction AX2 of the spring structure 420.

Furthermore, the inner surface of the positioning pin hole 316A can be a smooth structure. For example, the inner surface of the positioning pin hole 316A can be made smoother through surface treatment to improve the smoothness of the suture 50 passing through the positioning pin hole 316A.

However, the present disclosure is not limited thereto. As shown in FIG. 16, the edge of the positioning pin hole 416A of the plug cover 416 can be chamfered to have a chamfered structure RA, allowing the suture 50 to move along the curved configuration of the chamfered structure RA and improving the using convenience of suture stretching.

Figure 17:
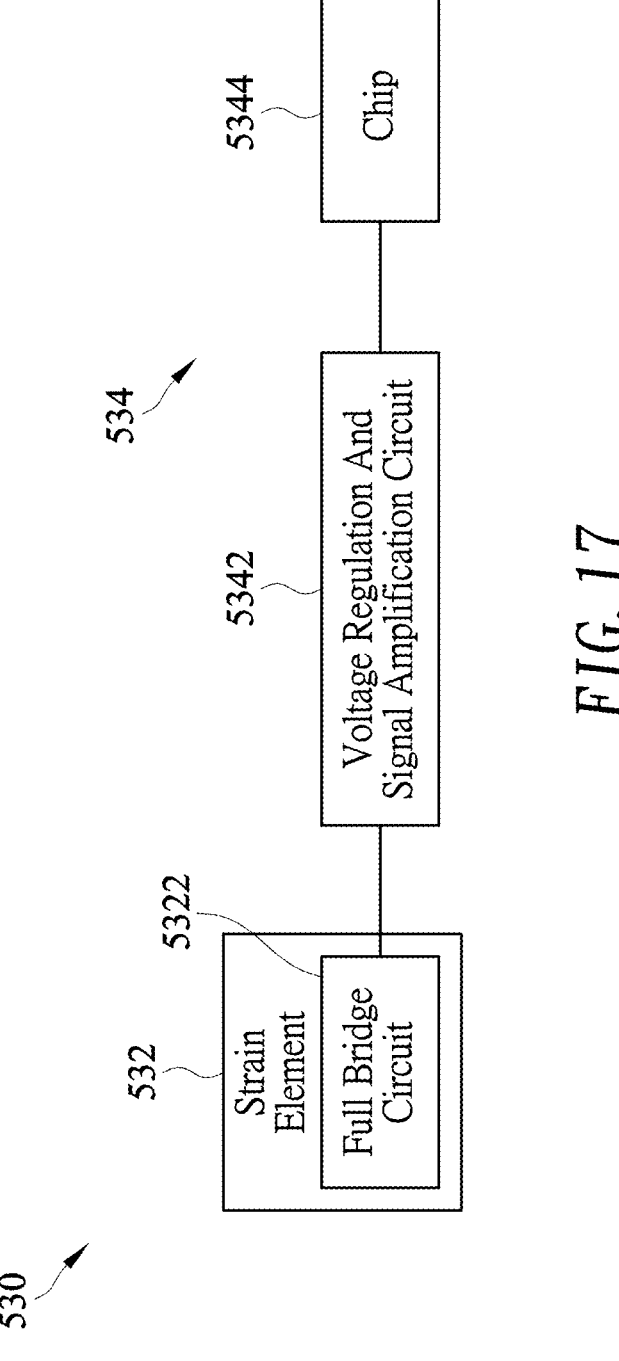
FIG. 17 is a schematic diagram of an embodiment of a detection module according to the present disclosure.
Figure 18:
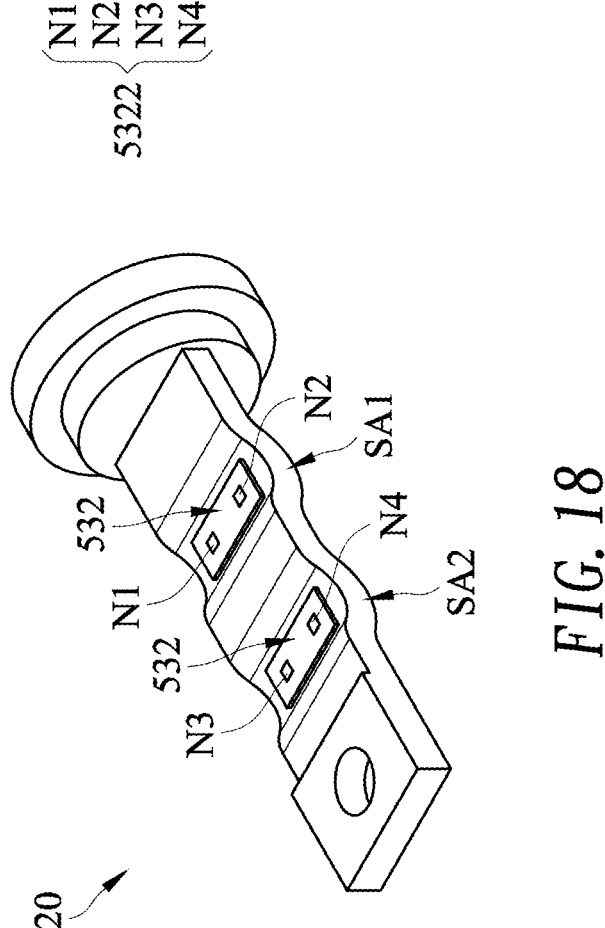
FIG. 18 is a schematic diagram of an embodiment of a full bridge circuit disposed on a spring structure according to the present disclosure.

FIG. 17 is a schematic diagram of an embodiment of a detection module according to the present disclosure. FIG. 18 is a schematic diagram of an embodiment of a full bridge circuit disposed on a spring structure according to the present disclosure. Please refer to FIGS. 17 and 18. The detection module 530 of the present disclosure includes a strain element 532 and a sensing component 534. The strain element 532 includes a full bridge circuit 5322.

The sensing component 534 includes a voltage regulation and signal amplification circuit 5342 and a chip 5344. The full bridge circuit 5322 is connected to the voltage regulation and signal amplification circuit 5342. The voltage regulation and signal amplification circuit 5342 is connected to the chip 5344. The chip 5344 may include an NFC chip (Near Field Communication chip) or RFID IC (Radio Frequency Identification Integrated Circuit, RFID Integrated Circuit), which cooperates with and connects the antenna module 140 and the hardware device 60 as shown in FIG. 1 to realize the battery-free function. Of course, in other embodiments, charging can be performed through an external power supply or other methods.

In one embodiment, in order to reduce the size or decrease the volume, the full bridge circuit 5322, the voltage regulation and signal amplification circuit 5342, and the chip 5344 can be designed into a module.

The full bridge circuit 5322 is, for example, a Wheatstone Bridge circuit, which is used to measure changes of physical quantities such as strain, temperature, pressure, etc., especially in the application of strain gauges and other sensors. As shown in FIG. 18, taking the spring structure 220 in FIG. 4 as an example, the two bending strain structures SA1 and SA2 are each provided with a strain element 532, and one strain element 532 is provided with two resistors N1 and N2 to form a half bridge circuit. Another strain element 532 is provided with two resistors N3 and N4 to form another half bridge circuit. Therefore, the two strain elements 532 have two half bridge circuits and four resistors N1, N2, N3, and N4. These four N1, N2, N3, and N4 will form a bridge structure to provide a full bridge circuit 5322. The above resistors N1, N2, N3, and N4 can be variable resistors (VRs). In other embodiments not shown, one, two, or four VRs can be set on a strain element according to the actual situation. If there are four VRs, a Wheatstone full bridge circuit can be formed.

By providing the above configuration, this embodiment can integrate the NFC chip or RFID IC and the strain element 532 including the full bridge circuit 5322, in order to achieve the goal of low power consumption (less than 1 mW).

Figure 19:
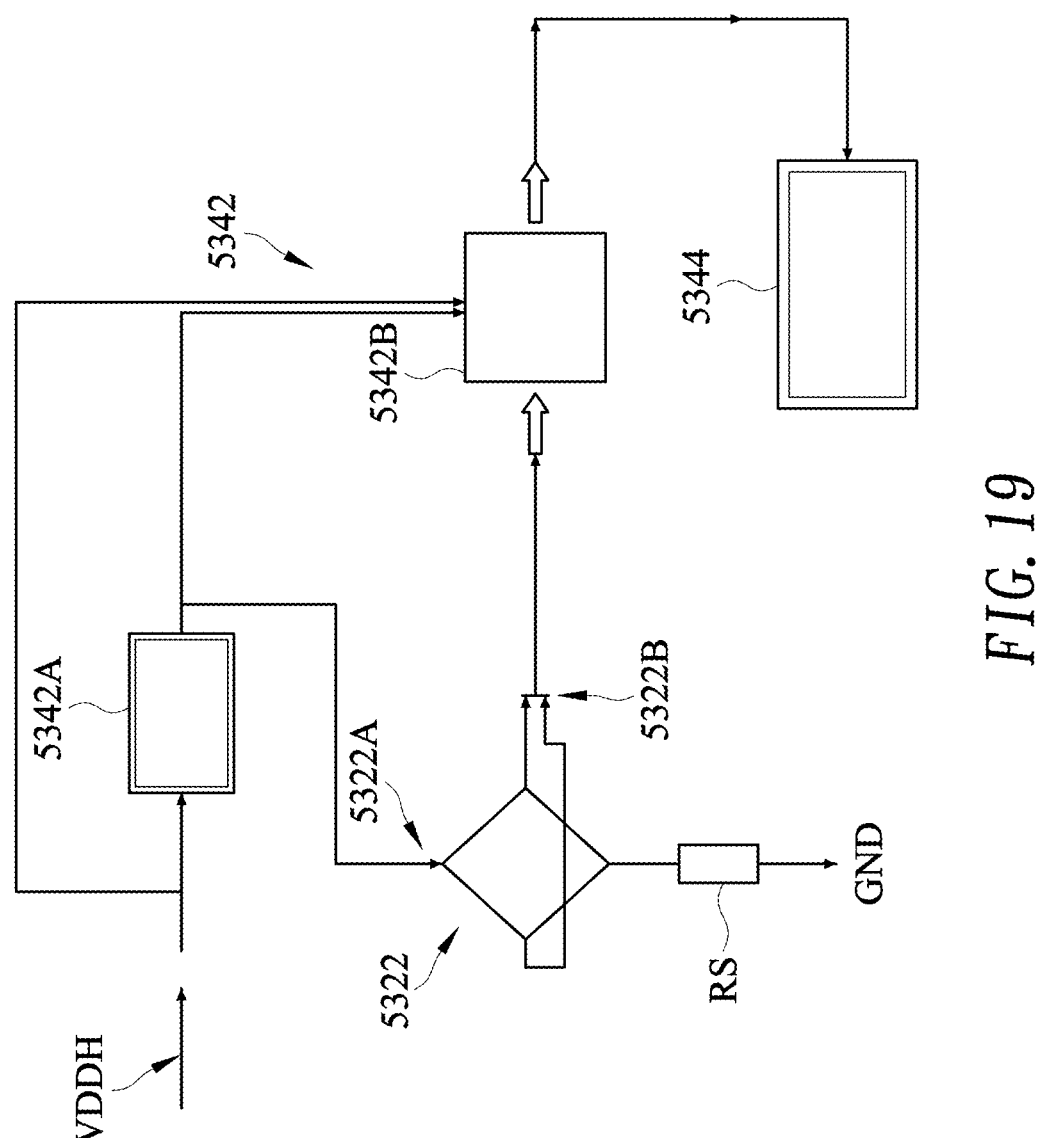
FIG. 19 is a schematic diagram of an embodiment of the sensing signal path and circuit design according to FIGS. 17 and 18.

FIG. 19 is a schematic diagram of an embodiment of the sensing signal path and circuit design according to FIGS. 17 and 18. Please refer to FIGS. 17 to 19. In this embodiment, the voltage regulation and signal amplification circuit 5342 is integrated into the aforementioned chip 5344 and the strain element 532 including the full bridge circuit 5322. The voltage regulation and signal amplification circuit 5342 is an amplifying circuit design, which includes a regulator 5342A and an instrumentation amplifier (INA) 5342B. The regulator 5342A is electrically connected to the INA 5342B, and the INA 5342B is electrically connected to the chip 5344. One end of the full bridge circuit 5322 is connected to a current limiting resistor RS. The current limiting resistor RS is, for example, 2900 ohms. One end of the current limiting resistor RS is the ground terminal GND. The purpose is to reduce the current. In this embodiment, the current limiting resistor RS is used to limit the current to 165 micro-Amp. The input terminal 5322A of the full bridge circuit 5322 is connected to the regulator 5342A, and the output terminal 5322B of the full bridge circuit 5322 is connected to the INA 5342B. With such circuit arrangement, the operating voltage VDDH is, for example, 1.9 volts of power input through RF induction. The input voltage modulation stabilization and signal gain amplification functions are performed through the regulator 5342A and the INA 5342B. In addition, the full bridge circuit 5322 inputs the voltage change value after conversion of the resistance value of the bending moment strain of the bending strain structure SA shown in FIG. 1 to the INA 5342B, and then transmits it to the chip 5344 after integration and conversion. The chip 5344 can have an analog-to-digital (ADC) conversion function, which can be converted into force data DA as shown in FIG. 1 and output to the external hardware device 60 through wireless transmission.

Based on the foregoing, when an external force is applied to the spring structure of the present disclosure, the spring structure will have displacement and deformation. By utilizing the structural characteristics of the bending strain structure, the detection module can calculate the applied force as force data according to the converted voltage change value of the bending moment strain of the corresponding bending strain structure, so as to evaluate whether the force data exceeds the load. Accordingly, the chance of re-tearing of the tendon after suturing can be avoided, and the degree of recovery at this time can be monitored to achieve the purpose of accelerating healing.

Furthermore, during the surgical operation, the present disclosure can be used as a monitoring mechanism to monitor the rivet implant during the surgical operation to avoid or reduce the failure of the rivet implant.

Moreover, in an embodiment of the present disclosure, in addition to deforming along the axial direction, the bending strain structure can also deform along at least one direction different from the axial direction. Accordingly, by having the structural characteristics of the bending strain structure, the small strain of the axial force of the spring structure along the axial direction can be converted into a larger bending moment strain. As such, the corresponding shape strains in the axial direction and at least one direction different from the axial direction can be provided, allowing the detection module to generate a signal corresponding to the force data that is large enough and linear, so as to improve detection quality and meet the needs of miniaturization of smart sensing implants.

In addition, one embodiment of the present disclosure uses polyetheretherketone (PEEK) as the material of the spring structure and the bone screw body. Regarding the smart sensing implant, PEEK's biocompatibility can be used safely in the human body.

In addition, the displacement of the spring structure using PEEK material can be proportional to the load data of the tension and has a linear relationship. In association with the structural characteristics of the bending strain structure, in addition to converting the small strain of the axial force for the spring structure being stretched into a larger bending moment strain, a signal corresponding to the force data can be generated that is large enough and linear, so as to greatly improve the detection quality.

Moreover, the axial direction of the spring structure of the present disclosure will pass through the positioning pin hole. The structural arrangement of the positioning pin hole and the positional conditions of the positioning pin hole and the spring structure enable the suture to exert force along the axial direction of the spring structure, limiting the tension of the suture on the axial direction of the spring structure. That is, the position of the positioning pin hole enables the force application conditions to be oriented and fixed, and solves the problem of non-axial component force.

Furthermore, in one embodiment of the present disclosure, the edge of the positioning pin hole of the plug cover can be chamfered to have a chamfered structure, allowing the suture to move along the curved configuration of the chamfered structure. Alternatively, surface treatment can be used so that the inner surface of the positioning pin hole is relatively smooth, improving the using convenience of suture stretching.

In addition, the present disclosure integrates NFC chip or RFID IC and the antenna module to realize the battery-free charging function.

Also, this embodiment can integrate the NFC chip or RFID IC, as well as the strain element and the full bridge circuit to achieve purpose of low power consumption (less than 1 mW).

In addition, the amplification circuit design is further integrated into the aforementioned NFC chip or RFID IC, as well as the strain element and full bridge circuit, and energy can be collected through external induction.

Although the present disclosure has been disclosed in the form of embodiments, they are not intended to limit the present disclosure. Anyone with ordinary knowledge in the relevant technical field may make slight changes and modifications without departing from the spirit and scope of the present disclosure. Therefore, the scope of protection of this disclosure shall be subject to the scope of the appended patent application.

The invention claimed is:

1. A force detection bone screw device used to detect a force of a suture, the force detection bone screw device comprising:
   a bone screw body, comprising a cylinder having an opening end and an insertion end opposite to each other, wherein an accommodating portion within the cylinder is connected with the opening end;
   a spring structure, provided in the accommodating portion, wherein the spring structure comprises a body, a bearing part, a fixing part, and at least one bending strain structure, one end of the body is connected to the bearing part, another end of the body is connected to the fixing part, the fixing part is fixed within the cylinder, the fixing part is adjacent to the insertion end, one side of the bearing part is used to connect to the suture, and each of the bending strain structures is respectively provided on the body, the body has an axial direction, and each of the bending strain structures has deformation in at least one direction different from the axial direction;
   a detection module, provided in the accommodating portion, wherein the detection module comprises at least one strain element and a sensing component, each of the strain elements is used to measure a stress of bending moment strain generated by the bending strain structure, and one end of the sensing component is connected to the strain element; and
   an antenna module, provided in the accommodating portion, and the antenna module is connected to the sensing component.

2. The force detection bone screw device according to claim 1, wherein each of the strain elements is disposed at a corresponding position of the corresponding bending strain structure in the body.

3. The force detection bone screw device according to claim 2, wherein the at least one bending strain structure has a concave surface and a convex surface opposite to each other, and the at least one strain element can be disposed on a location of one of the concave surface and the convex surface.

4. The force detection bone screw device according to claim 2, wherein the at least one bending strain structure is a concave structure or a bending structure of the body.

5. The force detection bone screw device according to claim 1, wherein the strain element is a strain gauge or a piezoelectric material structure.

6. The force detection bone screw device according to claim 1, wherein the bone screw body comprises a plug cover, the plug cover is provided with a positioning pin hole, and the axial direction of the spring structure passes through the positioning pin hole.

7. The force detection bone screw device according to claim 6, wherein a setting height position of the spring structure is the same as a setting height position of the positioning pin hole.

8. The force detection bone screw device according to claim 6, wherein an inner surface of the positioning pin hole is a smooth structure.

9. The force detection bone screw device as claimed in claim 6, wherein an edge of the positioning pin hole has a chamfered structure.

10. The force detection bone screw device according to claim 1, wherein the bone screw body comprises a plug cover, a turn-in structure is provided inside the cylinder close to the opening end, the turn-in structure is an inner hexagonal structure within the cylinder, the plug cover is located between the turn-in structure and the spring structure, and the plug cover comprises a suture through hole.

11. The force detection bone screw device according to claim 1, wherein the fixing part comprises an engaging element and a bottom element, the engaging element is connected between the body and the bottom element, the engaging element has an engaging structure, a protruding structure is provided within the cylinder, and the protruding structure is fixed to the engaging structure.

12. The force detection bone screw device according to claim 1, wherein a material of the spring structure is polyetheretherketone.

13. The force detection bone screw device as claimed in claim 1, wherein a material of the spring structure is a non-magnetic metal.

14. The force detection bone screw device according to claim 1, wherein a material of the bone screw body is polyetheretherketone.

15. The force detection bone screw device according to claim 1, wherein a material of the bone screw body is a non-magnetic metal.

16. The force detection bone screw device according to claim 1, wherein the bone screw body comprises a bottom cover, the bottom cover is disposed and closed at a bottom of the cylinder, and one side of the bottom cover is the insertion end.

17. The force detection bone screw device according to claim 16, wherein the cylinder is provided with a card groove structure, the bottom cover comprises an anti-rotation structure and a cover body, the anti-rotation structure is connected to the cover body, the anti-rotation structure is disposed inside the cylinder, and a side edge of the cover body is combined with the card groove structure.

18. The force detection bone screw device according to claim 1, wherein the bone screw body comprises a plurality of threads, and the threads are respectively protruding and disposed from an outer surface of the cylinder.

19. The force detection bone screw device according to claim 1, wherein each of the strain elements comprises a full bridge circuit.

20. The force detection bone screw device according to claim 19, wherein the sensing component comprises a voltage regulation and signal amplification circuit and a chip, the full bridge circuit is connected to the voltage regulation and signal amplification circuit, the voltage regulation and signal amplification circuit is connected to the chip, and the chip is connected to the antenna module.

21. The force detection bone screw device according to claim 20, wherein the voltage regulation and signal amplification circuit comprises a regulator and an instrumentation amplifier.

22. The force detection bone screw device according to claim 20, wherein the chip comprises an NFC chip.

* * * * *